(12) United States Patent
Chillon et al.

(10) Patent No.: US 11,714,017 B2
(45) Date of Patent: Aug. 1, 2023

(54) TEST UNIT AND PROCESS FOR MEASURING INTERNAL PRESSURE IN A CYLINDRICAL GLASS CONTAINER

(71) Applicant: Stevanato Group S.P.A., Piombino Dese (IT)

(72) Inventors: Alberto Chillon, Cadoneghe (IT); Barnaba Marchesini, Albignasego (IT)

(73) Assignee: Stevanato Group S.P.A., Piombino Dese (IT)

( * ) Notice: Subject to any disclaimer, the term of this patent is extended or adjusted under 35 U.S.C. 154(b) by 0 days.

(21) Appl. No.: 17/804,105

(22) Filed: May 26, 2022

(65) Prior Publication Data
US 2022/0381637 A1  Dec. 1, 2022

(30) Foreign Application Priority Data

May 26, 2021  (IT) .......................... 102021000013643

(51) Int. Cl.
| | |
|---|---|
| *G01L 27/00* | (2006.01) |
| *G01N 3/12* | (2006.01) |
| *G01L 1/02* | (2006.01) |
| *A61M 5/00* | (2006.01) |

(52) U.S. Cl.
CPC .............. *G01L 27/005* (2013.01); *G01N 3/12* (2013.01); *A61M 5/008* (2013.01); *A61M 2205/70* (2013.01); *G01L 1/02* (2013.01); *G01N 2203/04* (2013.01); *G01N 2203/0641* (2013.01)

(58) Field of Classification Search
CPC ........... G01L 27/005; G01L 1/02; G01N 3/12; G01N 2203/04; G01N 2203/0641; A61M 5/008; A61M 2205/70
See application file for complete search history.

(56) References Cited

U.S. PATENT DOCUMENTS

| | | |
|---|---|---|
| 2014/0288408 A1 | 9/2014 | Deutsch |
| 2017/0056604 A1* | 3/2017 | Cowan .............. A61M 5/14546 |

FOREIGN PATENT DOCUMENTS

AU  2005235438 B2  4/2011

\* cited by examiner

*Primary Examiner* — Ryan D Walsh
(74) *Attorney, Agent, or Firm* — Husch Blackwell LLP (57) ABSTRACT

A test unit for measuring internal pressure in a cylindrical glass container includes a support adapted for housing the cylindrical glass container during a test phase, defining a longitudinal axis; a piston for selectively exerting a predetermined axial force in a longitudinal direction substantially parallel to the longitudinal axis and for actuating a plunger movable along the longitudinal axis; at least one measuring sensor for measuring a change in diameter in a transverse direction to the longitudinal axis; a programmable control unit operatively connected to the measuring sensor and configured to correlate a diameter change measured by the measuring sensor in the presence of a predetermined axial force with reference internal pressure values to which the measured diameter change and the predetermined axial force correspond. Associated processes for measuring internal pressure in a cylindrical glass container are further disclosed.

15 Claims, 5 Drawing Sheets

TEST UNIT AND PROCESS FOR MEASURING INTERNAL PRESSURE IN A CYLINDRICAL GLASS CONTAINER

CROSS REFERENCES

This application claims priority to Italian Application No. 102021000013643 filed on May 26, 2021, the disclosure of which is expressly incorporated by reference herein in its entirety.

TECHNICAL FIELD

The present invention relates to a test unit and a method for measuring the internal pressure in a cylindrical glass container for pharmaceutical use. In particular, the present invention relates to a test unit and a method for measuring the pressure in a cylindrical glass container for pharmaceutical use, such as syringes, self-injection syringes or carpules.

BACKGROUND

As is well known, in cylindrical glass containers for pharmaceutical use there is a particular need to evaluate the internal pressure and the effects of a given internal pressure on the walls of the container itself.

In this disclosure, a cylindrical glass container is understood to be a substantially cylindrical container, in particular closed at one end or with a smaller opening at the end position, opposed to a plunger or pusher.

For example, self-injection syringes are arranged with a thrust system, typically a spring-loaded piston that, upon activation, acts on the plunger of the syringe to initiate the injection.

The spring, acting on the plunger, generates a pressure wave which propagates through the liquid contained within the syringe, causing an increase of the pressure inside the syringe; consequently, there is a pressurisation of the volume of liquid.

The pressure of the liquid contained in the syringe increases abruptly, in a time interval that can range from 0.1 to as much as 15 ms, but typically in about 0.15 to 3 ms, and equally abruptly stresses the walls of the syringe, which may break in rare cases.

The issue related to the increase of pressure within the syringe is more pronounced, for example, when concentrated and/or high viscosity drugs are contained, which may cause increased stresses at the syringe walls as a result of the necessary increase of the spring force to achieve acceptable injection times.

It is therefore known to subject syringes for self-injection to laboratory tests in which internal pressures of known magnitude are applied and relative wall deformations are measured.

Measurement of syringe wall deformation is generally accomplished by contact systems, typically a strain gauge, applied at a specific location on the outer surface of the syringe.

Once a known stress is applied to the syringe plunger, the internal pressure is detected (through dedicated internal sensors) and the relative wall deformation is measured using a strain gauge.

Although widely used and appreciated the known art is not without drawbacks. For example, the use of strain gauges makes the testing process particularly complicated and not suitable for random sampling in the production line.

In addition, the placement of strain gauges on the container wall is a time-consuming process, which is incompatible with the requirements of number of samples needed for production controls.

Furthermore, the test system of the prior art may be affected by problems due to a lack of precision in positioning the strain gauge. A positioning error can, for example, affect the measurement itself, but also the comparability of values measured on two different syringes. Indeed, the installation of strain gauges requires qualified personnel who are familiar with the problems associated with their installation (e.g., optimal amount of glue to be used).

In addition, the strain gauges, being attached to the outer wall of a syringe, cannot be reused (except by testing on the same syringe). In other words, the strain gauge cannot be removed and reused. This means using a number of strain gauges at least equal to the number of syringes to be tested, at the expense of costs and production times.

SUMMARY

There is therefore a need to resolve the drawbacks and limitations cited with reference to the known art.

Therefore, there is a need to provide a system that can also be used during in-line sampling or that is characterised by reasonably short measurement times.

In addition, there is a need for a system that is not affected by problems arising from inaccurate positioning of a measuring system on the outer surface of the container.

These requirements are fulfilled, at least in part, by a test unit for measuring the internal pressure in a cylindrical glass container in accordance with claim 1 and by a process for measuring the internal pressure in a cylindrical glass container in accordance with claim 13.

In particular, these requirements are at least partially fulfilled by a test unit for measuring the internal pressure in a cylindrical glass container that includes a support adapted for housing a cylindrical glass container during a test phase, so as to define a longitudinal axis (x), which, in use, corresponds to a longitudinal axis of a cylindrical glass container arranged in said support; piston adapted for selectively exerting a predetermined axial force in a longitudinal direction substantially parallel to said longitudinal axis (x), the piston being adapted for actuating a plunger movable along said longitudinal axis inside a container arranged in said support; at least one measuring sensor adapted for measuring a change in diameter in a transverse direction (y) which is transversal to said longitudinal axis (x); a programmable control unit operatively connected to said at least one measuring sensor and configured to correlate a diameter change measured by said at least one measuring sensor in the presence of a predetermined axial force with reference internal pressure values to which said measured diameter change and said predetermined axial force correspond.

According to an aspect of the present invention, the at least one measuring sensor is of an optical type.

According to a possible embodiment, said at least one measuring sensor comprises two measuring sensors arranged substantially opposite to each other in a diametrical direction.

In accordance with a possible embodiment, said at least one measuring sensor is arranged on an adjustable support adapted for adjusting the position of said at least one measuring sensor in a direction substantially parallel to the longitudinal direction and/or in a direction substantially parallel to the transverse direction (y).

In accordance with a possible embodiment, said at least one measuring sensor is adapted for measuring a change in diameter in a direction substantially perpendicular to said longitudinal axis (x).

According to a possible embodiment, said adjustable support is a micrometric slide that allows adjustment of the position along three Cartesian axes and adjustment by rotation about the three Cartesian axes.

According to a possible embodiment, the support is made of rigid or semi-rigid material.

According to a possible embodiment, said support is made of polymeric material, fibre-filled polymeric material, or aluminium.

In accordance with a possible embodiment, said support comprises a fixing base and a containment portion, said containment portion comprising a substantially cylindrical inner surface.

In accordance with a possible embodiment, said containment portion comprises at least one measuring aperture adapted for placing in visual communication the inside of the containment portion with the at least one measuring sensor.

In accordance with a possible embodiment, said containment portion comprises two diametrically opposed measuring apertures.

In accordance with a possible embodiment, said support is provided with longitudinal support means for supporting said cylindrical glass container.

In accordance with a possible embodiment, said longitudinal support means for supporting said cylindrical glass container may be adapted for supporting an intermediate portion of said container or an end portion thereof.

In accordance with a possible embodiment, the support is provided with a drainage hole adapted for ensuring the exit of fluid from the container following the impact of the piston.

In accordance with a possible embodiment, the drainage hole is arranged at the fixing base, so as to allow fluid communication between the outside and the inner surface of the containment portion.

According to a possible embodiment, said piston is of pneumatic, electric, or magnetic type.

According to a possible embodiment, said piston is arranged on a bridge-like support structure arranged on a first test bench on which said support is arranged.

In accordance with a possible embodiment, the test unit comprises a first test bench constituting a support for the piston and second test bench constituting a support unit for the at least one sensor, said first test bench and said second test bench being separate and/or vibrationally isolated from each other.

According to a possible embodiment, said control unit is configured to provide thrust values of the piston correlated with corresponding actual thrust values.

In accordance with a possible embodiment, when the cylindrical glass container is a self-injection syringe, the control unit is configured to provide thrust values of the piston correlated to corresponding actual thrust values of spring and piston of the self-injection syringe.

In accordance with a possible embodiment, the control unit is configured to make measurements at least in the range between 2 ms before the actuation of the plunger of the syringe and 30 ms after the actuation of the plunger of the syringe, preferably between 5 ms and 15 ms.

In accordance with a possible embodiment, the support comprises a force measuring device adapted for measuring the force applied by said piston on a syringe arranged in said support.

The process according to the present invention for measuring the internal pressure in a cylindrical glass container includes (a) an initial step of arranging a test unit for measuring internal pressure in a cylindrical glass container according to the above description; (b) a calibration step for calibrating said test unit, in which a determined type of cylindrical glass container is subjected to measurement, through the insertion of a pressure measuring device inside the container, in said calibration step predetermined axial forces being applied by said piston, each axial force value being correlated with a corresponding type of fluid contained inside the container, a corresponding variation of diameter of the container arranged in said support and a corresponding pressure value measured inside the container; (c) a step of measuring a change in diameter of a cylindrical glass container arranged in said support by means of at least one measuring sensor; (d) a processing step in which said programmable control unit operatively connected to said at least one measuring sensor correlates a diameter change measured by said at least one measuring sensor in the presence of a predetermined axial force with reference internal pressure values, measured in the calibration step, to which such measured diameter change and such predetermined axial force correspond.

In accordance with a possible embodiment, the process comprises a step prior to step (c) in which the at least one measuring sensor is positioned such that the angle α between the pointing trajectory of the measuring sensor and the tangent to the circumference at the observation point is 90°±10°, preferably 90°±5°, even more preferably 90°±1°.

In accordance with a possible embodiment, the process comprises a step prior to step (c) in which if the test unit is arranged with two measuring sensors the sensors are positioned so that the maximum misalignment between the measuring sensors in the longitudinal direction is 0.3 mm, preferably between 0.05 and 0.1 mm; and the maximum misalignment between the measuring sensors in the transverse direction is 0.3 mm, preferably between 0.05 and 0.1 mm.

In accordance with a possible embodiment, the process comprises a step prior to step (c) in which an observation point within at most 20 mm above the shoulder of the cylindrical glass container is selected, preferably in the region of 5 mm above the shoulder of the cylindrical glass container.

According to a possible embodiment, the calibration step comprises the following steps:
start of calibration;
installing strain gauges and/or installing pressure sensors;
comparing with measurements obtained by the measuring sensors;
verifying compliance with a mathematical model;
end of calibration.

According to a possible embodiment, the measurement step (c) comprises the steps of:
placing the container (100) in the support;
checking the vertical alignment between container and piston;
checking positioning of at least one measuring sensor;
starting data acquisition by the at least one measuring sensor;
piston actuation;
end of acquisition;

saving the collected data;

obtaining the maximum diameter variation by combining the signals coming from the at least one measuring sensor;

calculating the internal pressure at maximum diameter change using thick-shell theory in a linear elastic field; and obtaining the maximum diameter variation and the maximum theoretical reference pressure related to it in the calibration step.

BRIEF DESCRIPTION OF THE DRAWINGS

Further features and advantages of the present invention will be more readily understood from the following description of its preferred and non-limiting examples of embodiments, wherein.

Elements or portions of elements in common in the embodiments described below will be indicated by the same numerical references.

DETAILED DESCRIPTION

Figure 1:
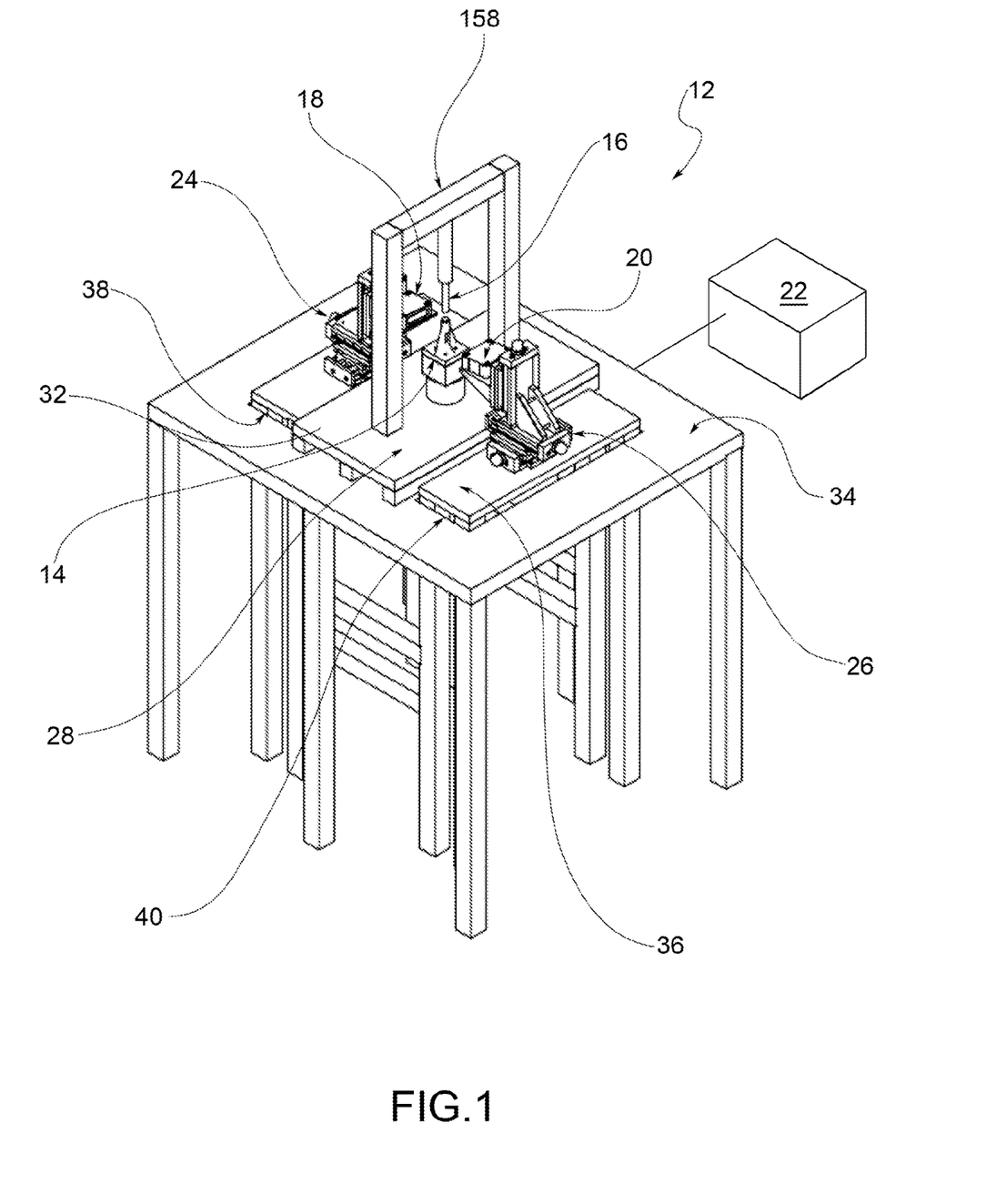
FIG. 1 depicts in schematic form a perspective view of a test unit according to an embodiment of the present invention.
Figure 2:
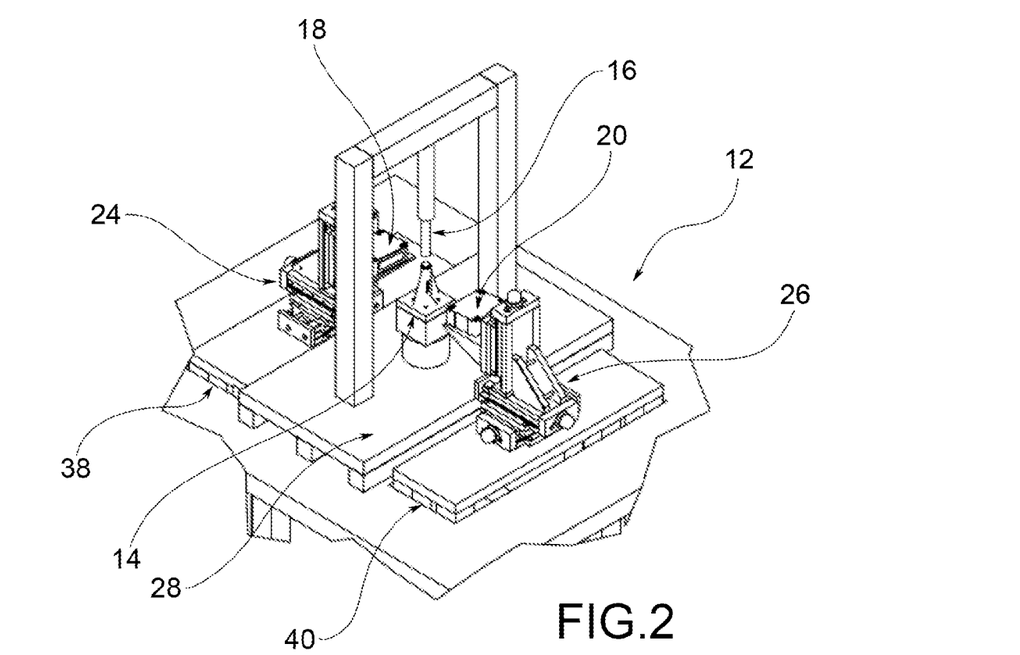
FIG. 2 depicts in schematic form a perspective view of a portion of a test unit according to an embodiment of the present invention.
Figure 3:
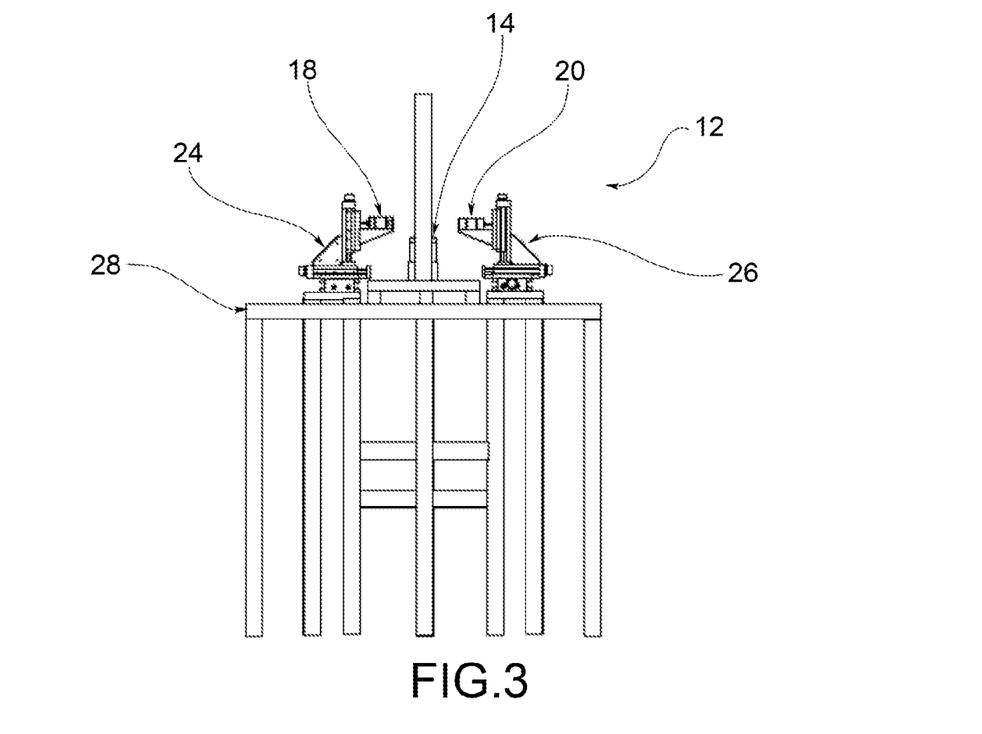
FIG. 3 depicts in schematic form a front view of a test unit according to an embodiment of the present invention.
Figure 4:
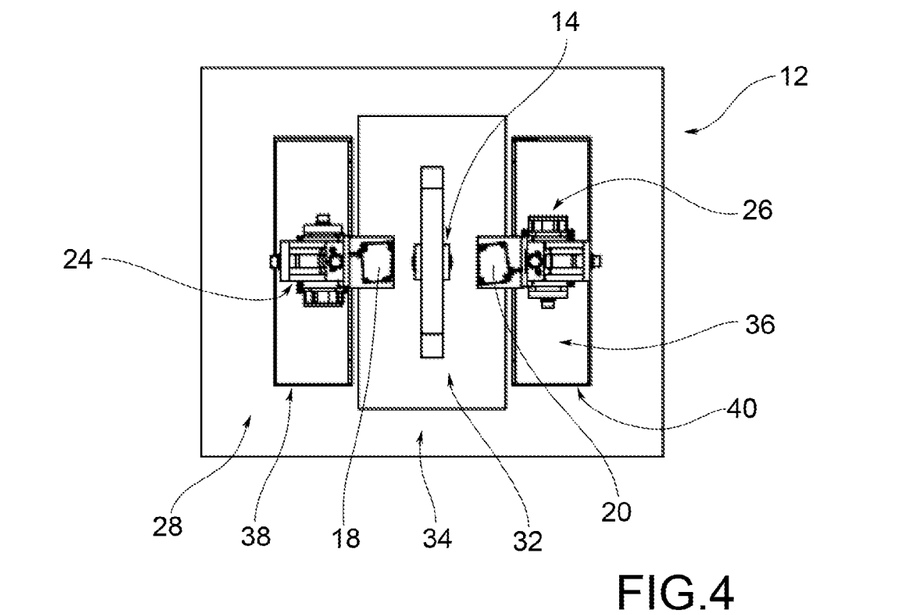
FIG. 4 depicts in schematic form a plan view from above of a test unit according to an embodiment of the present invention.
Figure 5:
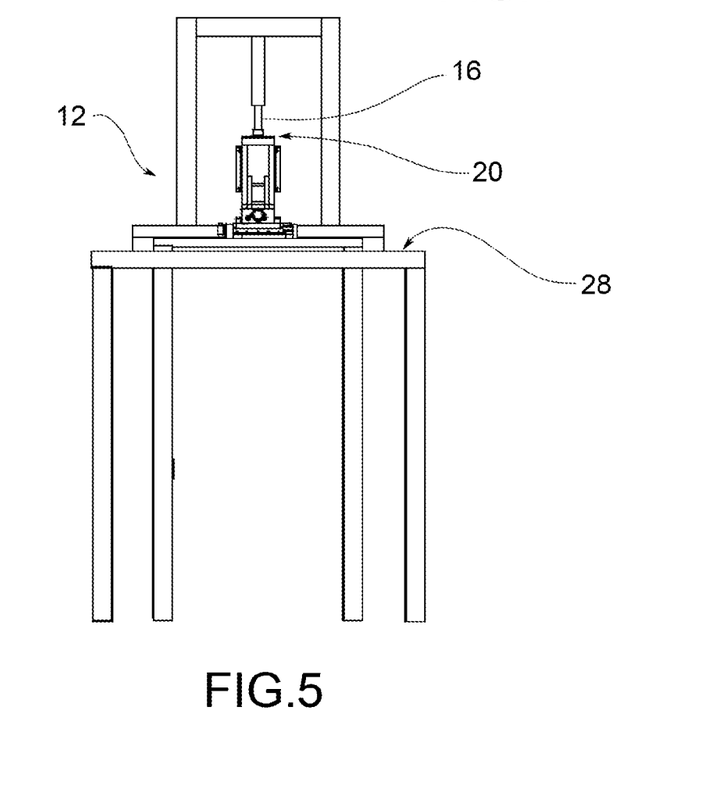
FIG. 5 depicts in schematic form a side view of a test unit according to an embodiment of the present invention.

In FIG. 1, reference 12 indicates a test unit for measuring the internal pressure in a cylindrical glass container 100.

The test unit 12 comprises a support 14 adapted for housing a cylindrical glass container 100 during a test phase, so as to define a longitudinal axis x which, in use, corresponds to a longitudinal axis of a cylindrical glass container 100.

Further, the test unit comprises a piston 16 adapted for selectively exerting a predetermined axial force in a longitudinal direction substantially parallel to the longitudinal axis x. The piston 16 is adapted for actuating a plunger 102 movable along the longitudinal axis inside a container 100 arranged in the support 14.

The test unit 12 further comprises at least one measuring sensor 18, 20, adapted for measuring a change in diameter in a transverse direction y which is transversal to the longitudinal axis x.

Furthermore, the test unit 12 comprises a programmable control unit 22 operatively connected to the at least one measuring sensor 18, 20 and configured to correlate a diameter change measured by the at least one measuring sensor 18, 20 in the presence of a predetermined axial force with reference internal pressure values to which such measured diameter change and such predetermined axial force correspond.

The at least one sensor 18, 20 can be of the optical type.

In accordance with a possible embodiment, the at least one sensor 18, 20 may be a laser-type sensor. For example, the at least one sensor 18, 20 may be a LH30IX485QP laser-type sensor marketed by Banner Engineering.

In accordance with a possible alternative embodiment, the at least one sensor 18, 20 may be a confocal-type sensor. For example, the at least one sensor 18, 20 can be a CHRocodile CLS confocal-type sensor marketed by the company Precitec.

The at least one measuring sensor 18, 20 may comprise two measuring sensors 18, 20 arranged substantially opposite to each other along a direction corresponding to a diametrical direction of the cylindrical glass container being tested or of a containment portion thereof.

In accordance with a possible embodiment, the at least one measuring sensor 18, 20 may be arranged on an adjustable support 24, 26 adapted for adjusting the position of the at least one measuring sensor 18, 20 in a direction substantially parallel to the longitudinal axis (x) and/or in a direction substantially parallel to the transverse direction (y).

The adjustable support 24, 26 may be, for example, a micrometric slide that allows adjustment of the position along at least one Cartesian axis, and adjustment by rotation about at least one of the Cartesian axes. Advantageously, the adjustable support 24, 26 may be a micrometric slide that allows position adjustment along three Cartesian axes, and adjustment by rotation about the three Cartesian axes.

According to a possible embodiment, the measuring sensors are adjusted in terms of position and signal strength by means of a dedicated computer program.

The adjustable support 24, 26 may be adapted to allow a positioning of the at least one measuring sensor 18, 20 such as to enable a measurement at the cylindrical glass container 100 between the shoulder 104 of the container and 2 cm in the direction of the plunger 102.

The support 14 may be made of rigid or semi-rigid material. According to a possible embodiment, the support 14 may be made of polymeric material, possibly reinforced with fibres. In alternative embodiments, the support 14 may be made of metal, e.g. aluminium.

Figure 6:
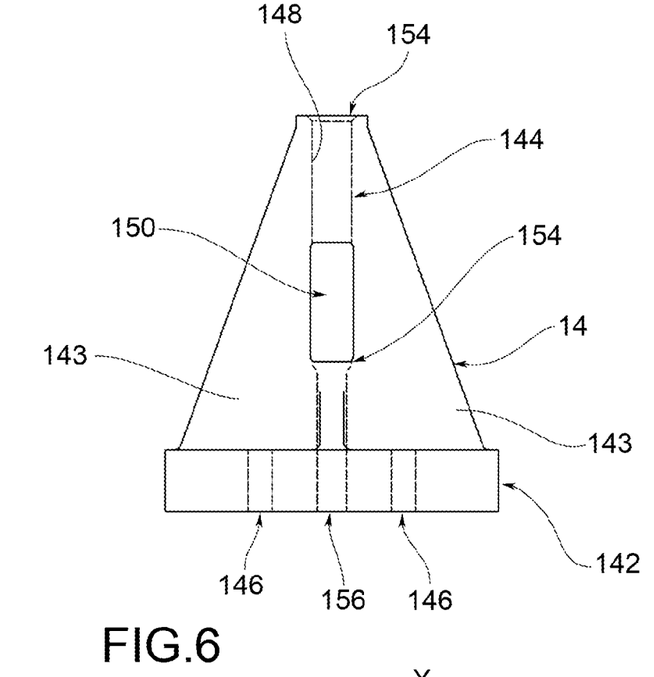
FIG. 6 depicts in schematic form a side view of a component of a test unit according to an embodiment of the present invention.
Figure 7:
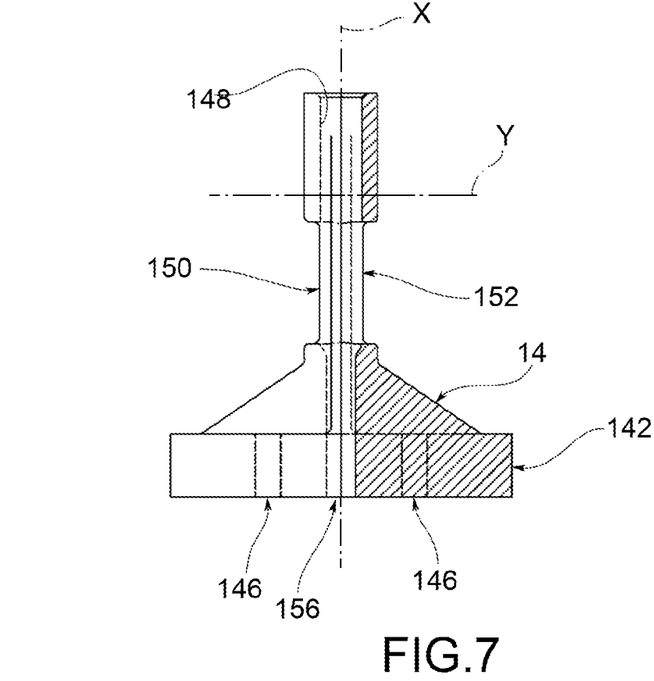
FIG. 7 depicts in schematic form a front view of a component of a test unit according to an embodiment of the present invention.

With reference to the embodiment of FIGS. 6 and 7, the support 14 may comprise a fixing base 142 and a containment portion 144.

The containment portion 144 of the support 14 may be adapted to prevent glass-to-glass or glass-to-metal contact, through the use of inserts (not shown) made of a polymeric material, arranged on the inner surface 148 of the containment portion 144 intended to accommodate the cylindrical glass container 100.

In accordance with a possible embodiment, the support 14 may be connected to a first test bench 28 for example by means of screws (not shown) and using through holes 146 provided at the fixing base 142.

The containment portion 144 may comprise a substantially cylindrical inner surface 148, at least one measuring aperture 150, 162 adapted for placing in visual communication the inside of the containment portion 144 with the at least one measuring sensor 18, 20.

The support 14 can be arranged with longitudinal support means 154 for supporting the cylindrical glass container 100.

The longitudinal support means 154 for supporting said cylindrical glass container may be adapted for supporting an intermediate portion of said container or an end portion.

For example, where the cylindrical glass container is a syringe, the longitudinal support means 154 may be adapted for supporting a shoulder area of the syringe, or a flange area.

Advantageously, the inner surface 148 of the support 14 may be counter-shaped with respect to the cylindrical glass container to be placed within it.

The inner surface 148 may be designed so that, in use, the distance between the inner surface 148 and the cylindrical glass container is less than 0.2 mm.

In accordance with a possible embodiment, the support 14 may be provided with a drainage hole 156 adapted for ensuring the exit of fluid from the container following the impact of the piston 16. The drainage hole 156 may be arranged at the fixing base 142 and so as to allow fluid communication between the outside and the inner surface 148 of the containment portion 144.

In accordance with a possible embodiment, stiffening wings 143 may be provided between the fixing base 142 and the containment portion 144, the stiffening wings 143 being adapted for making the containment portion 144 more stable with respect to the fixing base 142.

As can be seen in FIGS. 1-5, in accordance with a possible embodiment, the support 14, the piston 16 and the related support structure 158 can be arranged on a first test bench 28.

The first test bench 28 may have a substantially square base and be arranged with three legs on two opposite sides.

In accordance with a possible embodiment, the support 14, the piston 16 and the related support structure 158 may be arranged on a base structure 32 located above the support surface 34 of the first test bench 28.

In accordance with a possible embodiment, the measuring sensors 18, 20 are arranged on a second test bench 36, independent from the first test bench 28. Advantageously, the adjustable supports 24, 26 and thus the measuring sensors 18, 20 are arranged on a second test bench 36 independent from the first test bench 28.

In accordance with a possible embodiment, the support surface 34 of the first test bench 28 comprises at least one through opening 38, 40 from which said second test bench 36 protrudes with said at least one adjustable support 24, 26.

Advantageously, the support surface 34 of the first test bench 28 comprises two through openings 38, 40 from which said second test bench 36 protrudes with said adjustable supports 24, 26. The second test bench 36 can be divided into two separate benches so that each adjustable support 24, 26 is supported independently.

In this way, the first test bench 28 may be physically separated from the second test bench 36 so that any vibrations are not transmitted to the second test bench 36 on which the at least one measuring sensor 18, 20 is positioned.

In accordance with a possible embodiment, the first test bench 28 constituting a support for the piston (16) and the second test bench 36 constituting a support for the at least one sensor 18,20 may be separate and/or vibrationally isolated from each other.

In accordance with a possible embodiment, the support comprises a force measuring device 29 adapted for measuring the force applied by said piston on a syringe arranged in said support. The force measuring device can be provided, for example, on the support 14 or on a fixed part of the piston 16. Advantageously, the force measuring device can be a load cell, for example.

A process according to the present invention will be described below.

The process for measuring the internal pressure in a cylindrical glass container 100 comprises:
  an initial step of arranging a test unit 12 for measuring the internal pressure in a cylindrical glass container 100 having the characteristics described above;
  a calibration step of the test unit 12, in which a determined type of cylindrical glass container 100 is subjected to measurement, through the insertion of a pressure measuring device inside the cylindrical glass container 100, and predetermined axial forces are applied by the piston 16, each axial force value being correlated with a corresponding type of fluid contained inside the cylindrical glass container 100, a corresponding variation of diameter of the cylindrical glass container 100 arranged in the support 14 and a corresponding pressure value measured inside the cylindrical glass container 100;
  a step of measuring a change in diameter of a cylindrical glass container 100 arranged in the support 14 by means of at least one measuring sensor 18, 20;
  a processing step in which the programmable control unit 22 operatively connected to the at least one measuring sensor 18, 20 correlates a diameter change measured by the at least one measuring sensor 18, 20 in the presence of a predetermined axial force with reference internal pressure values to which such measured diameter change and such predetermined axial force correspond.

In other words, in the case of a syringe for self-injection, the piston 16 of the test unit 12 simulates the spring-piston system that activates the plunger 102.

In accordance with a possible embodiment, the impact speed of the piston 16 may be adjusted to achieve substantially the same impact force as the spring-piston system activating the plunger 102. In this case, due to a lower mass of the syringe spring-piston system with respect to the piston 16, the impact speed of the piston 16 on the plunger 102 will be lower.

A possible process for positioning a measuring sensor 18, 20, preparatory to measurement step (c), will be described below.

Figure 8:
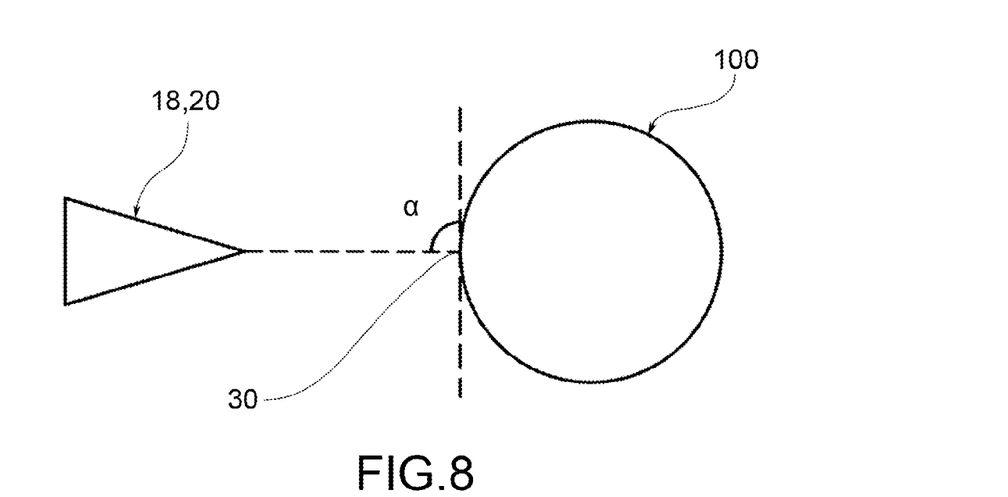
FIGS. 8 and 9 schematically depict a plan view from above and a front view of the relative arrangement between a container and a component of the test unit according to an embodiment of the invention.
Figure 9:
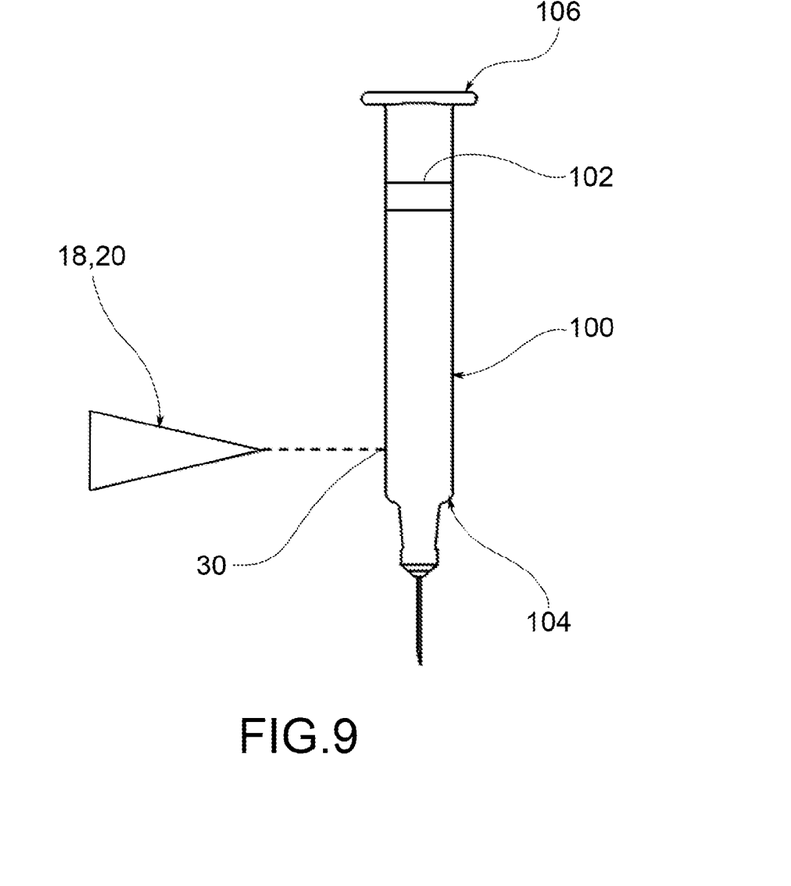

Once the point of interest on which the measurement is to be made has been established, and thus the circumference of the container 12 whose diameter is to be measured has been identified, the measuring sensor 18, 20 is pointed so as to measure this distance, i.e. at the point closest to the sensor itself (as seen in the example shown in FIGS. 8 and 9).

As can be seen in FIG. 8, the angle $\alpha$ between the pointing trajectory of the measuring sensor 18, 20 and the tangent to the circumference at the observation point 30 can be 90°±10°, preferably 90°±5°, even more preferably 90°±1°.

In case the test unit 12 is prepared with two measuring sensors 18, 20:
  the maximum misalignment between them in the longitudinal direction maybe 0.3 mm, preferably between 0.05 and 0.1 mm; and
  the maximum misalignment between them in the transverse direction may be 0.3 mm, preferably between 0.05 and 0.1 mm.

In accordance with a possible embodiment, the observation point 30 may be selected around 5 mm above the shoulder.

The distance between the measuring sensor 18, 20 and the observation point 30 can be decided according to the distance which creates the highest strength of the acquired signal. Advantageously, the control unit 22 can be adapted to display the signal strength in order to adjust the position and thus the distance of the measuring sensor 18, 20 with respect to the container 100.

The calibration step (b) can be performed with pressure sensors and strain gauges.

As mentioned above, the measuring sensors allow the variation of the diameter of the outer wall of the container due to the impact of the piston with the plunger to be obtained.

Strain gauges can be used to obtain a deformation measurement of the outer wall of the container in both axial and circumferential directions. Pressure sensors, on the other hand, allow direct measurement of the internal pressure.

In a way that is known, changes in diameter (measured with non-contact measuring sensors), deformations (measured with strain gauges) and internal pressures (measured with pressure sensors) can be correlated by the linear theory of thick shells assuming a uniaxial state of tension in the circumferential direction. Considering that the model used is linear-elastic, increasing the change in diameter linearly increases the internal pressure.

The peak of the diameter changes obtained with the measurement sensors were validated by comparison with peak deformation values obtained from measurements with strain gauges and pressure sensors, for different piston impact speeds.

Calibration can then be carried out directly by the user, e.g. by means of a predetermined procedure.

Calibration can be performed by placing the strain gauges at the observation point 30 of the measuring sensor 18, 20.

The step of validating the models used can be carried out taking into account various types of containers 12 and parameters, such as: different filling volumes of the container, viscosity of the liquid used, presence or absence of air gap, different types of springs.

Advantageously, the use of two measuring sensors 18, 20 makes it possible to evaluate the diameter variation net of system vibrations, translations, bending of the container.

According to a possible embodiment, the calibration step may comprise the following steps:
start of calibration;
installing strain gauges and/or installing pressure sensors;
comparing with measurements obtained by the measuring sensors 18, 20;
verifying compliance with the mathematical model;
end of calibration.

According to a possible embodiment the measurement step (c) may comprise the steps of:
placing the container 100 in the support 14;
checking the vertical alignment between container 100 and piston 16;
checking the positioning of at least one measuring sensor 18, 20;
starting data acquisition by the at least one measuring sensor 18, 20;
piston actuation 16;
end of acquisition;
saving the collected data (e.g. in a table in csv or similar format);
obtaining the maximum diameter variation by combining the signals coming from the at least one measuring sensor 18, 20;
calculating the internal pressure at the maximum diameter change using thick-shell theory in a linear elastic field; and
output: the maximum diameter variation and the maximum theoretical reference pressure related to it in the calibration step.

Thus, the advantages that can be obtained with the test unit and the process according to the present invention are now apparent.

Firstly, the method makes an indirect measurement of the internal pressure in a container by measuring the change in diameter.

In addition, a test unit and a process have been made available which allow a non-contact measurement of the internal pressure in a cylindrical glass container.

In this way, the test unit can for example be provided directly in a production line, since there is no need for operations to be performed manually by operators, such as the application of strain gauges in the processes of the prior art.

At the same time, the system is not affected by problems related to the positioning of strain gauges on the outer surface of the container. Accordingly, the measurement carried out with the test unit and the process of the present invention can be easy repeated, and measurements can be compared between containers of the same type.

In order to meet specific requirements, the skilled person may make modifications and or substitutions of described elements with equivalent elements in the embodiments described above, without thereby departing from the scope of the appended claims.

What is claimed is:

1. A test unit for measuring internal pressure in a cylindrical glass container, comprising:
a support adapted for housing the cylindrical glass container during a test phase, so as to define a longitudinal axis;
a piston adapted for selectively exerting a predetermined axial force in a longitudinal direction substantially parallel to said longitudinal axis, the piston being adapted for actuating a plunger within the cylindrical glass container movable along said longitudinal axis;
at least one measuring sensor, adapted for measuring a change in diameter of the cylindrical glass container in a transverse direction which is transversal to said longitudinal axis;
a programmable control unit operatively connected to said at least one measuring sensor and configured to correlate a diameter change measured by said at least one measuring sensor in the presence of a predetermined axial force with reference internal pressure values to which said measured diameter change and said predetermined axial force correspond.

2. The test unit according to claim 1, wherein said at least one measuring sensor is an optical sensor.

3. The test unit according to claim 1, wherein said at least one measuring sensor comprises two measuring sensors arranged substantially opposite to each other in a diametrical direction.

4. The test unit according to claim 1, wherein said at least one measuring sensor is arranged on an adjustable support adapted for adjusting the position of said at least one measuring sensor in a direction substantially parallel to the longitudinal direction and/or in a direction substantially parallel to the transverse direction.

5. The test unit according to claim 1, wherein said at least one measuring sensor is adapted for measuring a change in diameter of the cylindrical glass container in a direction substantially perpendicular to said longitudinal axis.

6. The test unit according to claim 1, wherein said support comprises a fixing base and a containment portion, said containment portion comprising a substantially cylindrical inner surface and at least one measuring aperture adapted for placing in visual communication the inside of the containment portion with the at least one measuring sensor.

7. The test unit according to claim 6, wherein the support is provided with a drainage hole adapted for ensuring the exit of fluid from the cylindrical glass container following the impact of the piston, said drainage hole being arranged at the fixing base, so as to allow fluid communication between the outside and the inner surface of the containment portion.

8. The test unit according to claim 1, wherein said support is provided with longitudinal support means for supporting said cylindrical glass container and adapted for supporting an intermediate portion of said container or an end portion thereof.

9. The test unit according to claim 1, further comprising a first test bench constituting a support for the piston and second test bench constituting a support unit for the at least one measuring sensor, said first test bench and said second test bench being separate and/or vibrationally isolated from each other.

10. The test unit according to claim 1, wherein said programmable control unit is configured to provide thrust values of the piston correlated with corresponding actual thrust values.

11. The test unit according to claim 1, wherein the programmable control unit is configured to make diameter measurements at least in the range between 2 ms before the actuation of the plunger and 30 ms after the actuation of the plunger.

12. The test unit according to claim 1, wherein said support comprises a force measuring device adapted for measuring the force applied by said piston on the plunger.

13. A process for measuring internal pressure in a cylindrical glass container comprising:
(a) an initial step of arranging a test unit for measuring internal pressure in a cylindrical glass container according to claim 1;
(b) a calibration step for calibrating said test unit, in which a determined type of cylindrical glass container is subjected to measurement through the insertion of a pressure measuring device inside the container, in said calibration step predetermined axial forces being applied by said piston, each axial force value being correlated with a corresponding type of fluid contained inside the container, a corresponding variation of diameter of the container arranged in said support and a corresponding pressure value measured inside the container;
(c) a step of measuring a change in diameter of a cylindrical glass container arranged in said support by means of at least one measuring sensor;
(d) a processing step in which said programmable control unit operatively connected to said at least one measuring sensor correlates a diameter change measured by said at least one measuring sensor in the presence of a predetermined axial force with reference internal pressure values, measured in the calibration step, to which such measured diameter change and such predetermined axial force correspond.

14. The process for measuring internal pressure in a cylindrical glass container according to claim 13, wherein the calibration step comprises the following steps:
start of calibration;
installing strain gauges and/or installing pressure sensors;
comparing with measurements obtained by the at least one measuring sensor;
verifying compliance with a mathematical model;
end of calibration.

15. The process for measuring internal pressure in a cylindrical glass container according to claim 13, wherein the measuring step (c) comprises the steps of:
placing the cylindrical glass container in the support;
checking a vertical alignment between the cylindrical glass container and the piston;
checking positioning of the at least one measuring sensor;
starting data acquisition by the at least one measuring sensor;
actuating the piston;
completing data acquisition by the at least one measuring sensor;
collecting and saving data acquired by the at least one measuring sensor;
obtaining a maximum diameter variation from the collected and saved data acquired by the at least one measuring sensor;
calculating the internal pressure at a maximum diameter change using thick-shell theory in a linear elastic field; and
obtaining the maximum diameter variation and a maximum theoretical reference pressure related to it in the calibration step.

* * * * *